US008262703B2

(12) United States Patent
Prakash et al.

(10) Patent No.: US 8,262,703 B2
(45) Date of Patent: Sep. 11, 2012

(54) MEDICAL DEVICE INCLUDING MEMBER THAT DEPLOYS IN A SPIRAL-LIKE CONFIGURATION AND METHOD

(75) Inventors: Mani N. Prakash, Boulder, CO (US); Tao D. Nguyen, Redwood City, CA (US)

(73) Assignee: Vivant Medical, Inc., Boulder, CO (US)

( * ) Notice: Subject to any disclaimer, the term of this patent is extended or adjusted under 35 U.S.C. 154(b) by 780 days.

(21) Appl. No.: 12/353,617

(22) Filed: Jan. 14, 2009

(65) Prior Publication Data

US 2009/0198226 A1    Aug. 6, 2009

Related U.S. Application Data

(60) Provisional application No. 61/025,124, filed on Jan. 31, 2008.

(51) Int. Cl.
| A61B 17/70 | (2006.01) |
| A61B 18/04 | (2006.01) |
| A61B 17/56 | (2006.01) |
| A61B 17/58 | (2006.01) |
| A61F 2/30  | (2006.01) |

(52) U.S. Cl. ............................. 606/261; 606/28; 606/78
(58) Field of Classification Search .............. 606/27–34, 606/41–42, 261, 78
See application file for complete search history.

(56) References Cited

U.S. PATENT DOCUMENTS

| 3,631,363 A | 12/1971 | Miller |
| 4,397,313 A | 8/1983 | Vaguine |
| 4,462,412 A | 7/1984 | Turner |
| 4,572,190 A | 2/1986 | Azam et al. |
| 4,798,215 A | 1/1989 | Turner |
| 5,057,106 A | 10/1991 | Kasevich et al. |
| 5,097,844 A | 3/1992 | Turner |
| 5,275,597 A | 1/1994 | Higgins et al. |
| 5,370,675 A | 12/1994 | Edwards et al. |
| 5,417,210 A | 5/1995 | Funda et al. |
| 5,500,012 A | 3/1996 | Brucker et al. |
| 5,536,240 A | 7/1996 | Edwards et al. |
| 5,683,382 A | 11/1997 | Lenihan et al. |
| 5,800,494 A | 9/1998 | Campbell et al. |
| 5,871,523 A | 2/1999 | Fleischman et al. |
| 5,897,554 A | 4/1999 | Chia et al. |
| 5,902,251 A | 5/1999 | vanHooydonk |
| 5,980,563 A | 11/1999 | Tu et al. |

(Continued)

FOREIGN PATENT DOCUMENTS

DE     390937     3/1924

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Nicholas Lucchesi
*Assistant Examiner* — Rebecca E Eisenberg

(57) ABSTRACT

A medial device including a handle portion, and a deployable member disposed in mechanical cooperation with the handle portion is disclosed. The deployable member includes a distal tip and a bend that is disposed adjacent the distal tip. The deployable member is extendable form the handle portion such that the distal tip extends in a spiral-like configuration in response to extension of the deployable member. The spiral-like configuration includes non-equivalent radii.

27 Claims, 5 Drawing Sheets

U.S. PATENT DOCUMENTS

| | | | |
|---|---|---|---|
| 6,001,093 | A | 12/1999 | Swanson et al. |
| 6,016,811 | A | 1/2000 | Knopp et al. |
| 6,022,346 | A | 2/2000 | Panescu et al. |
| 6,031,375 | A | 2/2000 | Atalar et al. |
| 6,052,607 | A | 4/2000 | Edwards et al. |
| 6,056,744 | A | 5/2000 | Edwards |
| 6,071,281 | A | 6/2000 | Burnside et al. |
| 6,146,379 | A | 11/2000 | Fleischman et al. |
| 6,217,528 | B1 | 4/2001 | Koblish et al. |
| 6,241,725 | B1 | 6/2001 | Cosman |
| 6,246,912 | B1 | 6/2001 | Sluijter et al. |
| 6,251,128 | B1 | 6/2001 | Knopp et al. |
| 6,287,302 | B1 | 9/2001 | Berube |
| 6,375,606 | B1 | 4/2002 | Garibaldi et al. |
| 6,419,653 | B2 | 7/2002 | Edwards et al. |
| 6,506,189 | B1 | 1/2003 | Rittman, III et al. |
| 6,511,478 | B1 | 1/2003 | Burnside et al. |
| 6,527,768 | B2 | 3/2003 | Berube |
| 6,603,994 | B2 | 8/2003 | Wallace et al. |
| 6,610,054 | B1 | 8/2003 | Edwards et al. |
| 6,622,731 | B2 | 9/2003 | Daniel et al. |
| 6,652,515 | B1 | 11/2003 | Maguire et al. |
| 6,699,241 | B2 | 3/2004 | Rappaport et al. |
| 6,725,080 | B2 | 4/2004 | Melkent et al. |
| 6,786,905 | B2 | 9/2004 | Swanson et al. |
| 6,852,091 | B2 | 2/2005 | Edwards et al. |
| 6,878,147 | B2 | 4/2005 | Prakash et al. |
| 6,942,661 | B2 | 9/2005 | Swanson |
| 6,997,925 | B2 | 2/2006 | Maguire et al. |
| 7,128,739 | B2 | 10/2006 | Prakash et al. |
| 7,147,632 | B2 | 12/2006 | Prakash et al. |
| 7,186,251 | B2 | 3/2007 | Malecki et al. |
| 7,197,363 | B2 | 3/2007 | Prakash et al. |
| 7,252,665 | B2 | 8/2007 | Starkebaum et al. |
| 7,282,050 | B2 | 10/2007 | Starketbaum et al. |
| 7,300,438 | B2 | 11/2007 | Falwell et al. |
| 7,303,558 | B2 | 12/2007 | Swanson |
| 7,309,336 | B2 | 12/2007 | Ashley et al. |
| 7,311,705 | B2 | 12/2007 | Sra |
| 7,318,824 | B2 | 1/2008 | Prakash et al. |
| 7,326,201 | B2 | 2/2008 | Fjield et al. |
| 7,335,196 | B2 | 2/2008 | Swanson et al. |
| 7,387,626 | B2 | 6/2008 | Edwards et al. |
| 7,439,736 | B2 | 10/2008 | Meaney et al. |
| 7,467,015 | B2 | 12/2008 | Van der Weide |
| 7,565,207 | B2 | 7/2009 | Turner et al. |
| 2002/0022836 | A1 | 2/2002 | Goble et al. |
| 2003/0158549 | A1 | 8/2003 | Swanson |
| 2003/0195499 | A1 | 10/2003 | Prakash et al. |
| 2004/0097805 | A1 | 5/2004 | Verard et al. |
| 2004/0242992 | A1 | 12/2004 | Hareyama |
| 2005/0010095 | A1 | 1/2005 | Stewart et al. |
| 2005/0228370 | A1 | 10/2005 | Sterzer et al. |
| 2006/0015162 | A1 | 1/2006 | Edwards et al. |
| 2006/0106375 | A1 | 5/2006 | Werneth et al. |
| 2006/0259024 | A1 | 11/2006 | Turovskiy et al. |
| 2006/0264923 | A1 | 11/2006 | Prakash et al. |
| 2006/0282069 | A1 | 12/2006 | Prakash et al. |
| 2006/0293650 | A1 | 12/2006 | Prakash et al. |
| 2007/0016180 | A1 | 1/2007 | Lee, Jr. et al. |
| 2007/0129721 | A1 | 6/2007 | Phan et al. |
| 2007/0198006 | A1 | 8/2007 | Prakash et al. |
| 2007/0219546 | A1 | 9/2007 | Mody et al. |
| 2007/0219551 | A1 | 9/2007 | Honour et al. |
| 2007/0250051 | A1* | 10/2007 | Gaston et al. ................ 606/33 |
| 2007/0276362 | A1 | 11/2007 | Rioux et al. |
| 2007/0293853 | A1 | 12/2007 | Truckai et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 070 518 | 1/2001 |
| EP | 1 159 926 | 5/2001 |
| EP | 1 186 274 | 3/2002 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | 94/04220 | 3/1994 |
| WO | WO97/41924 | 11/1997 |
| WO | WO97/43971 | 11/1997 |
| WO | WO00/48672 | 8/2000 |
| WO | WO00/51513 | 9/2000 |
| WO | WO01/01847 | 1/2001 |

| WO | WO01/74252 | 10/2001 |
| WO | WO02/45790 | 6/2002 |
| WO | WO02/061880 | 8/2002 |
| WO | 03/088858 | 10/2003 |
| WO | WO2004/112628 | 12/2004 |
| WO | WO2005/016119 | 2/2005 |
| WO | 2007/112081 | 10/2007 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8. 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula. Popper & Sons Biomedical Instrument Division, (Products Price List), one page. Jul. 19, 2000.
Anonymous. Ground Cannulae. ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47. No. 5. Aug. 2002, p. 41.
C. F. Gottlieb et al., "Interstitial Microwave Hyperthermia Applicators having Submillimetre Diameters", Int. J. Hyperthermia, vol. 6, No. 3. pp. 707-714. 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw Hill, vol. 111, (1984). pp. 2490-2499.
Crawford et al., "Use of the LigaSure™ Vessel Sealing System in Urologic Cancer Surger" Grand Rounds in Urology 1999, vol. 1, Issue 4, pp. 1 0-17.

Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline Product Literature, "Light Key: Visualize a Virtual Keyboard. One With No Moving Parts", 4 pages, 2003.

Esterline, "Light Key Projection Keyboard" 2004 Advanced Input Systems, located at: <http://www.advanced-input.com/lightkey> last visited on Feb. 10, 2005.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6. No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al.. (1995) "Saline-enhanced RF Tissue Ablation in the Treatment of Liver Metastases", Radiology, pp. 205-210.

Lyndon B. Johnson Space Center. Houston, Texas. "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies". Thermoradiotheray and Thermochemotherapy (1995) vol. I. Biology, Physiology. Physics, pp. 279-320.

Palazzo et al., "Randomized clinical trial of LigaSure™ versus open haemorrhoidectomy" British Journal of Surgery 2002.89.154-157 "Innovations in Electrosurgery" Sales/Product Literature: Dec. 31, 2000.

Paul G. Horgan, "A Novel Technique for Parenchymal Division During Hepatectomy" The American Journal of Surgery, vol. 181, No. 3, Oapril 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure. "Kleppinger Bipolar Forceps & Bipolar Generator" 3 pages, Jan. 1989.

Rothenberg et al.. "Use of the LigaSure™ Vessel Sealing System in Minimally Invasive Surgery in Children" Int'l Pediatric Endosurgery Group (1 PEG) 2000.

Sayfan et al., "Sutureless Closed Hemorrhoidectomy: A New Technique" Annals of Surgery, vol. 234, No. 1, Jul. 2001, pp. 21-24.

Sengupta et al.. "Use of a Computer-Controlled Bipolar Diathermy System in Radical Prostatectomies and Other Open Urological Surgery" ANZ Journal of Surgery (2001)71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques. vol. 44. No. 10. pp. 1832-1840. Oct. 1995.
T. Matsukawa et al., "Percutaneous Microwave Coagulation Therapy in Liver Tumors", Acta Radiologica, vol. 38. pp. 410-415, 1997.
T. Seki et al., (1994) "Ultrasonically Guided Percutaneous Microwave Coagulation Therapy for Small Hepatocellular Carcinoma," Cancer 74(3):817.825.
S. Humphries Jr. et al., "Finite-Element Codes to Model Electrical Heating and Non-Llnear Thermal Transport in Biological Media", Proc. ASFM HTD-355, 131 (1997).
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report Ep 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
European Search Report 09151736.7 dated Jun. 12, 2009.

* cited by examiner

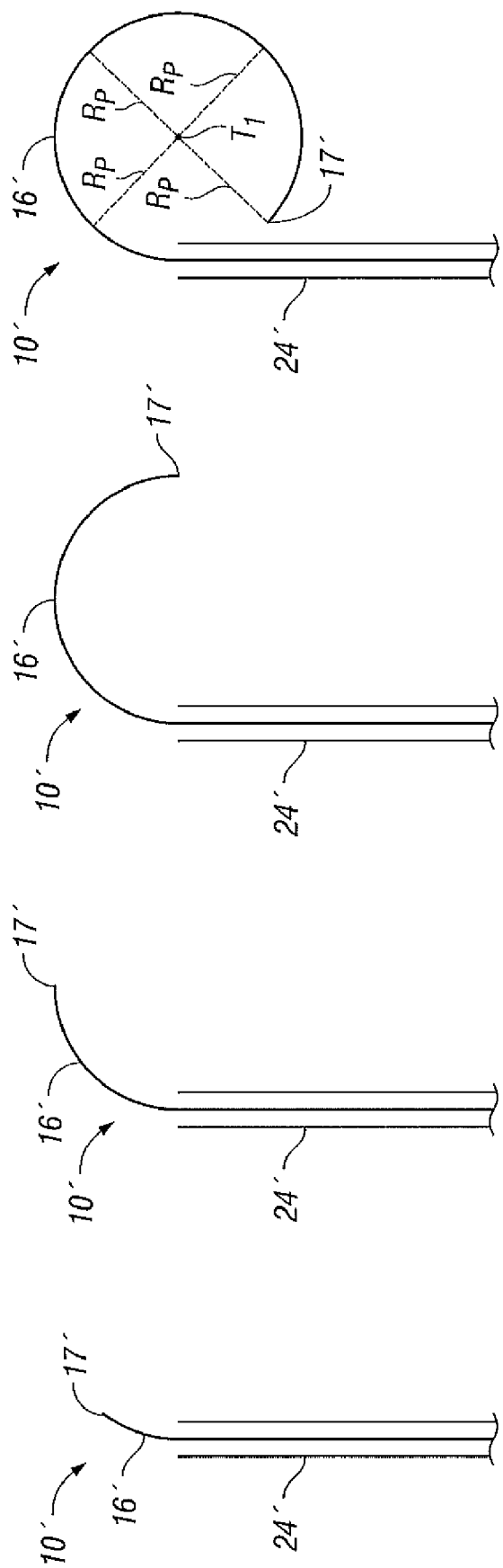

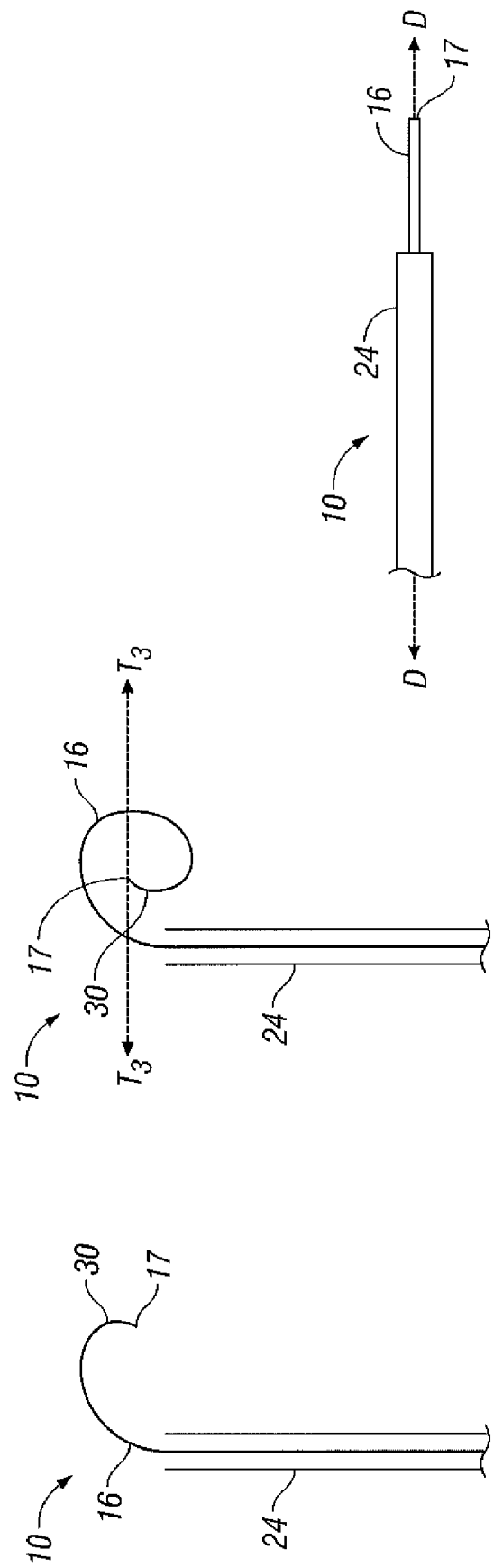

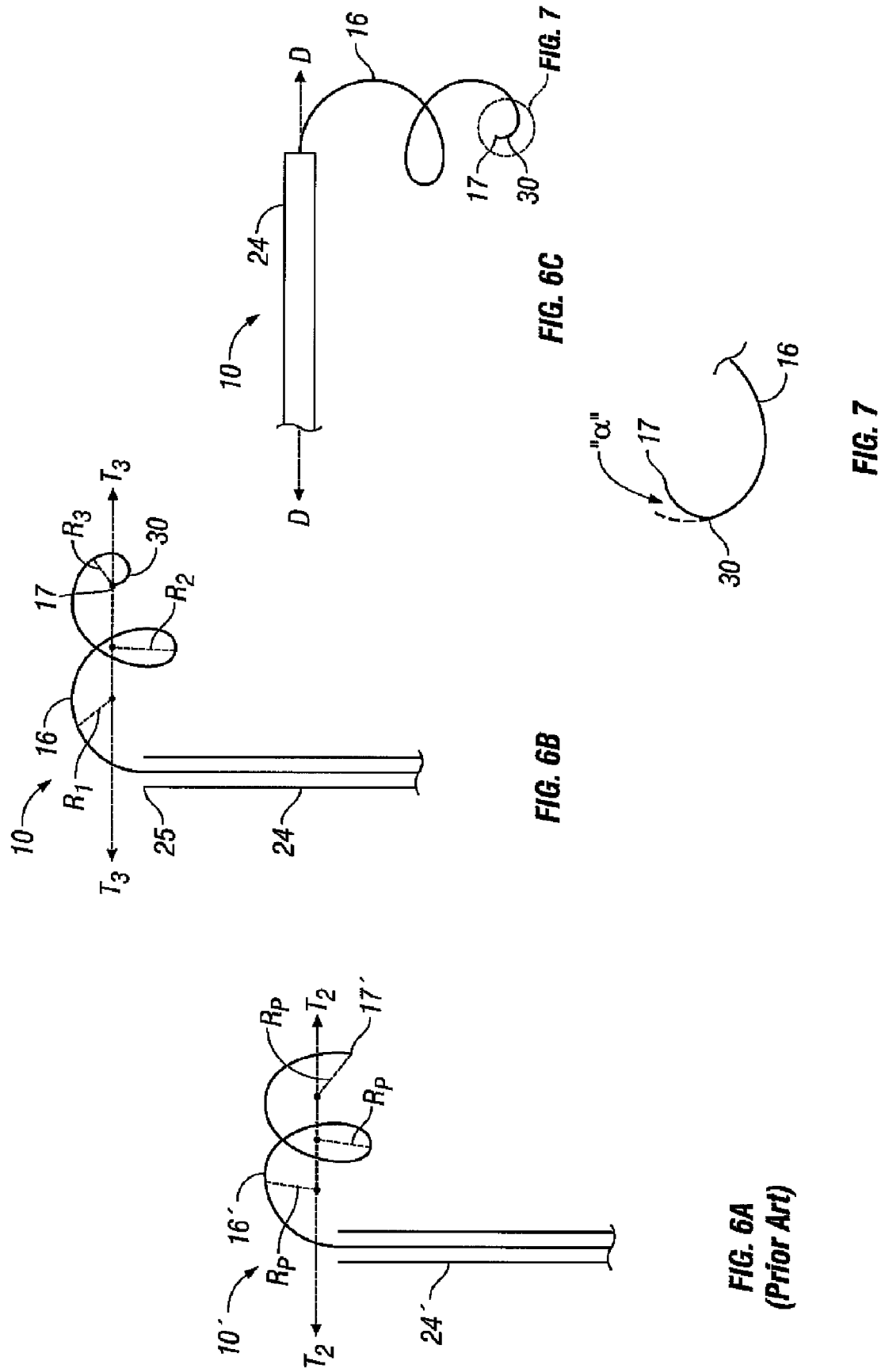

MEDICAL DEVICE INCLUDING MEMBER THAT DEPLOYS IN A SPIRAL-LIKE CONFIGURATION AND METHOD

CROSS-REFERENCE TO RELATED APPLICATIONS

This application claims the benefit of priority to U.S. Provisional Application Ser. No. 61/025,124 entitled "MEDICAL DEVICE INCLUDING MEMBER THAT DEPLOYS IN A SPIRAL-LIKE CONFIGURATION AND METHOD" filed Jan. 31, 2008 by Mani N. Prakash et al, which is incorporated by reference herein.

BACKGROUND

1. Technical Field

The present disclosure relates to medical devices and methods. More particularly, the disclosure relates to medical devices, such as microwave ablation devices, including a member that deploys in a spiral-like configuration.

2. Background of Related Art

In the treatment of diseases such as cancer, certain types of cancer cells have been found to denature at elevated temperatures that are slightly lower than temperatures normally injurious to healthy cells. These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great amount of control. This is partly why a more direct and precise method of applying microwave radiation has been sought.

Presently, there are several types of microwave probes in use, e.g., monopole, dipole, and helical. One type is a monopole antenna probe consisting of a single, elongated microwave conductor exposed at the end of the probe. The probe is sometimes surrounded by a dielectric sleeve. The second type of microwave probe commonly used is a dipole antenna consisting of a coaxial construction having an inner conductor and an outer conductor with a dielectric separating a portion of the inner conductor and a portion of the outer conductor. In the monopole and dipole antenna probe, microwave energy generally radiates perpendicularly from the axis of the conductor.

Because of the perpendicular pattern of microwave energy radiation, conventional antenna probes are typically designed to be inserted directly into the tissue, e.g., a tumor, to be radiated. However, such typical antenna probes commonly fail to provide uniform heating axially and/or radially about the effective length of the probe.

It is often difficult to assess the extent to which the microwave energy will radiate into the surrounding tissue, i.e., it is difficult to determine the area or volume of surrounding tissue that will be ablated. Furthermore, when conventional microwave antennas are inserted directly into the tissue, e.g., cancerous tissue, there is a danger of dragging or pulling cancerous cells along the antenna body into other parts of the body during insertion, placement, or removal of the antenna probe.

One conventional method for inserting and/or localizing wires or guides includes a wire guide that is delivered into breast tissue, for example, through a tubular introducer needle. When deployed, the wire guide cuts into and scribes a circular path about the tissue distal to a lesion while the remainder of the distal portion of the wire guide follows the path scribed by the distal tip and locks about the tissue.

SUMMARY

The present disclosure relates to a medial device including a handle portion, and a deployable member disposed in mechanical cooperation with the handle portion. The deployable member includes a distal tip and a bend that is disposed adjacent the distal tip. The deployable member is extendable form the handle portion such that the distal tip extends in a spiral-like configuration in response to extension of the deployable member. The spiral-like configuration includes non-equivalent radii.

The present disclosure also relates to an ablation device including a handle portion, an inner conductor extending distally from the handle portion and an outer conductor surrounding the inner conductor. The inner conductor includes a length, a proximal portion, a distal tip and a bend disposed adjacent the distal tip. The outer conductor extends at least partially along the length of the inner conductor and defines a longitudinal axis. At least the distal tip of the inner conductor is extendable distally beyond a distal-most end of the outer conductor. The distal tip extends in a spiral-like configuration in response to extension of the inner conductor, and the spiral-like configuration includes non-equivalent radii.

The present disclosure also relates to a method of treating tissue. The method includes providing an ablation device including a handle portion, an inner conductor extending distally form the handle portion and an outer conductor surrounding the inner conductor. The inner conductor includes a length, a proximal portion, a distal tip and a bend disposed adjacent the distal tip. The outer conductor extends at least partially along the length of the inner conductor and defines a longitudinal axis. The method also includes the step of extending the distal tip of the inner conductor beyond a distal-most end of the outer conductor such that the distal tip extends in a spiral-like configuration having non-equivalent radii.

The present disclosure also relates to an ablation device for treating tissue. The ablation device includes an outer conductor defining a longitudinal axis, a dielectric material retained within the outer conductor and an inner conductor slidably supported within the dielectric material. The inner conductor is slidable from a distal end of the outer conductor and a distal end of the dielectric material. A distal portion of the inner conductor is biased to a spiral-like configuration having a varying radius along an entire length thereof.

DESCRIPTION OF THE DRAWINGS

Embodiments of the presently disclosed medical devices are disclosed herein with reference to the drawings, wherein:

FIGS. 4A-4D are top views of a distal portion of a microwave ablation device of the prior art in various stages of deployment;

FIGS. 5A and 5B are tops views of a distal portion of the microwave ablation device of FIG. 1 in various stages of deployment;

FIG. 5C is a side view of the distal portion of the microwave ablation device of FIG. 5B;

FIG. 6A is a top view of a distal portion of a microwave ablation device of the prior art;

FIGS. 6B and 6C are top and side views, respectively, of a distal portion of the microwave ablation device of FIGS. 1-3 and 5A-5C; and FIG. 7 is an enlarged side view of the distal portion of the microwave ablation device of FIG. 6C.

DETAILED DESCRIPTION OF EMBODIMENTS

Figure 1:
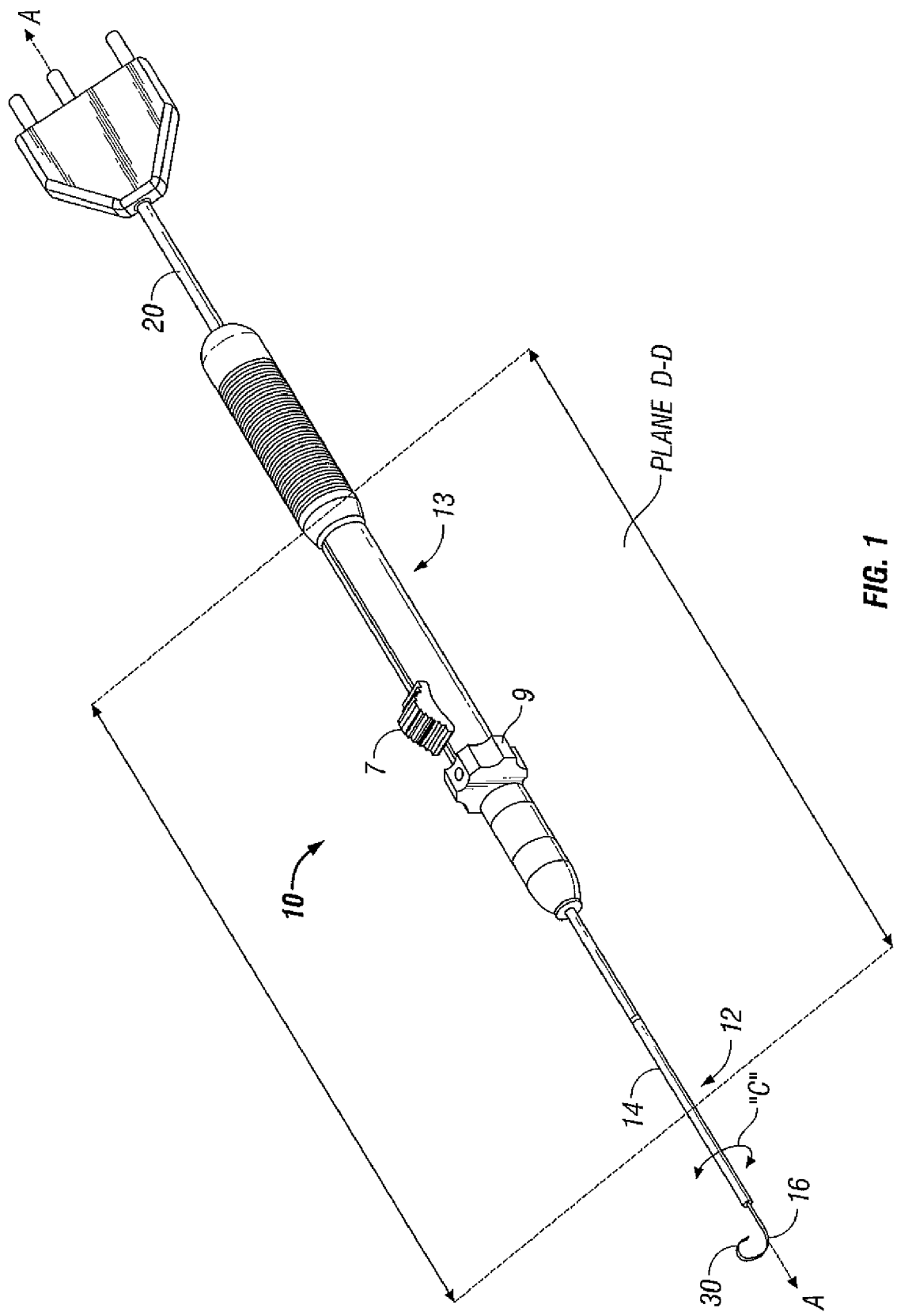
FIG. 1 is a perspective view of a microwave ablation device in accordance with an embodiment of the present disclosure.

Embodiments of the presently disclosed medical devices are described in detail with reference to the drawings, in which like reference numerals designate identical or corresponding elements in each of the several views. As used herein the term "distal" refers to that portion of the medical device, or component thereof, farther from the user while the term "proximal" refers to that portion of the medical device or component thereof, closer to the user.

Figure 2:
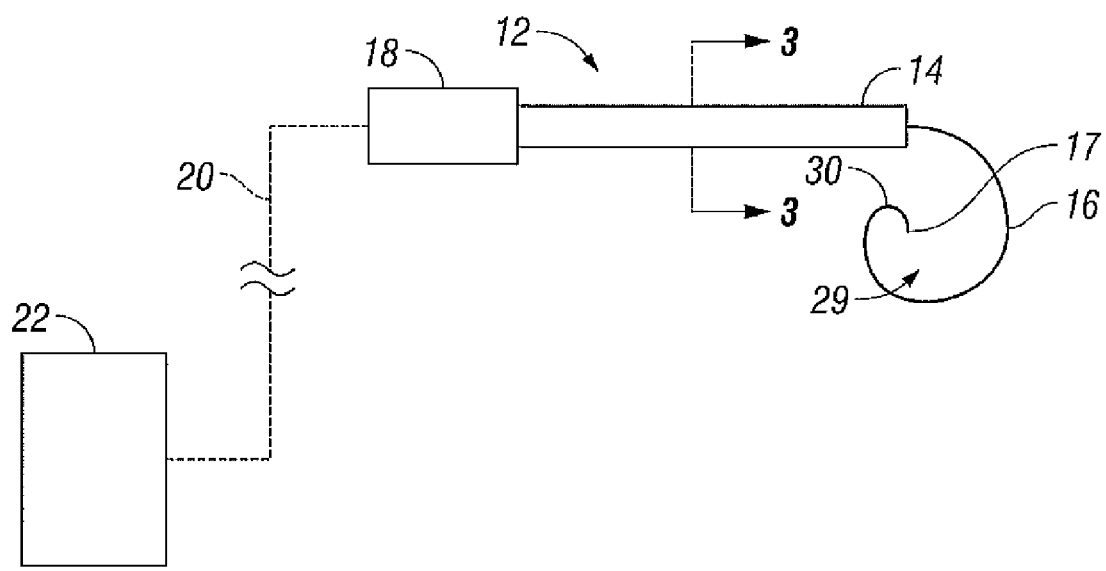
FIG. 2 is a schematic view of the microwave ablation device of FIG. 1 connected to a supply.

A medical device in accordance with the present disclosure is referred to in the figures as reference numeral 10. While the figures depict medical device 10 as an ablation device (e.g., a microwave ablation device), it is envisioned that medical device 10 includes any suitable instrument that includes a deployable member (e.g., a device for delivering radiofrequency, ultrasound, cryotherapy energy, laser energy, fluid (such as chemotherapeutic agents) and/or material). Referring initially to FIG. 1, microwave ablation device 10 includes a microwave antenna 12 and a handle portion 13. Microwave antenna 12 includes a shaft or feedline 14 having a deployable member or inner conductor 16. A supply line 20 is shown to connect microwave ablation device 10 to a suitable supply 22 (e.g., an electrosurgical generator, a supply of fluid, etc.) (FIG. 2). Additionally, an actuation element 7 and a rotation knob 9 are illustrated in FIG. 1 in accordance with various embodiments of the present disclosure.

As seen in FIG. 2, inner conductor 16 is extendable from feedline 14 to define an ablation region 29. In the embodiments where energy (e.g., electrosurgical energy) is delivered (e.g., radiofrequency, ultrasound, cryotherapy energy, laser energy, etc.), the proximal end of feedline 14 includes a coupler 18 which electrically couples antenna 12 to a generator or supply 22 via a power transmission cord or supply line 20. In the embodiments where fluid or material is delivered (e.g. chemotherapeutic agents), the feedline 14 is in fluid cooperation with a fluid reservoir or supply 22 via a suitable means for transporting fluid (e.g., tube, hose, etc.) or supply line 20.

With reference back to FIG. 1, actuation element 7 is shown disposed in mechanical cooperation with handle portion 13 and connected (not shown) to inner conductor 16. As can be appreciated, distal and proximal translation of actuation element 7, with respect to handle portion 13, causes corresponding translation of inner conductor 16 for deployment and/or retraction out of or into feedline 14. Further, it is understood that inner conductor 16 is translatable with respect to an outer conductor 24 and a dielectric 28 (see FIG. 3).

In accordance with an embodiment of the present disclosure, the connection between rotation knob 9 and inner conductor 16 allows inner conductor 16 to be rotated about a longitudinal axis A-A defined by outer conductor 24, as indicated by arrow "C" of FIG. 1. Additionally, while still allowing rotation of inner conductor 16, the connection with rotation knob 9 permits inner conductor 16 to be translated distally and proximally, as discussed above. It is envisioned that inner conductor 16 and feedline 14 are configured with respect to each other such that rotation of inner conductor 16 is enabled when inner conductor 16 is deployed.

As can be appreciated, the combination of the rotation of inner conductor 16 and the spiral-like configuration of inner conductor 16 upon deployment (as discussed in greater detail below), allows a distal tip 17 of inner conductor 16 to be positioned at a multitude of positions adjacent and/or at least partially surrounding a desired tissue region. Distal tip 17 of inner conductor 16 is disposed at an extreme end of inner conductor 16, as illustrated in FIGS. 2, 5A-5C, 6B, 6C and 7. Accordingly, microwave ablation device 10 provides a great deal of versatility during laparoscopic, endoscopic, endoluminal, and transluminal procedures. Device 10 may be capable of delivering radiofrequency (RF), microwave (MW), laser, ultrasound and cryotherapy energy. The ablative properties of device 10 may be enhanced by delivery of fluids (e.g., alcohol, chemotherapeutic agents, saline, electrolytic fluid, etc.) to the treatment site.

It is envisioned that microwave ablation device 10 may be introduced to the treatment site via a straight, arcuate, non-deployable and/or deployable applicator or introducer.

As described above and as shown in FIG. 3, feedline 14 may be a coaxial cable. Portions of feedline 14 may be formed of an outer conductor 24 surrounding an inner conductor 16. Conductors 16 and 24 may be made of a suitable conductive metal that may be semi-rigid or flexible, such as, for example, copper, gold, or other conductive metals with similar conductivity values. Alternatively, portions of conductors 16 and 24 may also be made from stainless steel that may additionally be plated with other materials, e.g., other conductive materials, to improve their properties, e.g., to improve conductivity or decrease energy loss, etc.

For example, an inner conductor 16 made of stainless steel may have an impedance of about 50Ω. In order to improve a conductivity of stainless steel inner conductor 16, inner conductor 16 may be coated with a layer of a conductive material such as copper or gold. Although stainless steel may not offer the same conductivity as other metals, it does offer increased strength required to puncture tissue and/or skin.

Figure 3:
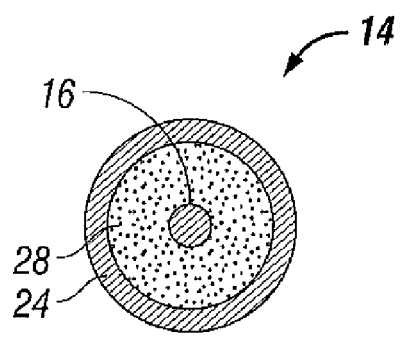
FIG. 3 is a cross-sectional view of a portion of a feedline of the microwave ablation device of FIGS. 1 and 2, as taken through 3-3 of FIG. 2.

With continued reference to FIG. 3, feedline 14 of antenna 12 includes dielectric 28 surrounding at least a portion of a length of inner conductor 16, and an outer conductor 24 surrounding at least a portion of a length of dielectric 28 and/or inner conductor 16. That is, a dielectric material 28 is interposed between inner and outer conductors 16, 24, respectively, to provide insulation therebetween and may be comprised of any appropriate variety of conventional dielectric materials.

In FIGS. 4A-4D, a distal end of a prior art microwave ablation device 10' is shown illustrating inner conductor 16' extending from outer conductor 24' at various stages of deployment. As illustrated, inner conductor 16' is articulated such that inner conductor 16' defines a rounded shape having a substantially consistent radius $R_p$. Here, distal tip 17' of inner conductor 16' is caused to be moved or articulated towards the right or an opposite direction. In so doing, inner conductor 16' is moved or articulated from a first position, where distal tip 17' is substantially aligned with an axis defined by its handle portion, to at least a second position where distal tip 17' is disposed at an angle relative to the axis.

In this prior art embodiment of microwave ablation device 10', areas of tissue disposed adjacent center line $T_1$ (illustrated as a point $T_1$ in FIG. 4D, which extends through the page) are not contacted by inner conductor 16'.

Referring to FIGS. 1, 2, 5A, 5B, 6B, 6C and 7, microwave ablation device 10 of the present disclosure is shown where inner conductor 16 includes a bend 30 disposed adjacent distal tip 17. It is envisioned that a portion of inner conductor 16 disposed proximal of bend 30 and a portion of inner conductor 16 disposed distal of bend 30 form an angle "α" of between about 5° and about 25° (See FIG. 7). For clarity, an extension of inner conductor 16 is shown as a dashed line, which illustrates the projected curve of inner conductor 16 if it lacked bend 30. The inclusion of bend 30 causes inner conductor 16 to extend in a spiral-like configuration having inconsistent radii when deployed in tissue, for instance. That is, the initial path of inner conductor 16 is determined by the shape of its distal end (including bend 30). As the deployment progresses, a shape memory of the proximal portion of inner conductor 16 (the portion closest to a distal-most end 25 of outer conductor 24) develops and leads to a curve with a smaller radius at the distal portion of inner conductor 16 (adjacent distal tip 17).

With reference to FIGS. 5A-5C, inner conductor 16 of ablation device 10 is shown extended in a planar (e.g., two-dimensional), spiral-like configuration, as it is disposed on substantially the same plane D-D (FIGS. 1, 5C and 6C) as handle portion 13. Here, distal tip 17 is biased in a single direction (e.g., by bending distal tip 17 to the right). In this embodiment, distal tip 17 of inner conductor 16 extends towards the right (in FIG. 5A) upon initial deployment of inner conductor 16. Continued deployment of inner conductor 16 causes distal tip 17 to continue its movement in a spiral-like configuration (FIG. 5B).

Referring to FIG. 6A, a microwave ablation device 10' of the prior art is shown. Here, inner conductor 16' extends from outer conductor 24' in a circular configuration and having a constant radius $R_p$. As can be appreciated, areas of tissue disposed adjacent center line $T_2$-$T_2$ are not contacted by inner conductor 16'.

FIGS. 6B and 6C illustrate another embodiment of microwave ablation device 10, in accordance with the present disclosure. Here, inner conductor 16 is shown extending in a non-planar, spiral-like configuration wherein radii $R_1$-$R_3$ are inconsistent or non-equivalent (FIG. 6B) and wherein the radii decrease as distal tip 17 moves farther from distal-most end 25 of outer conductor 24. Additionally, as seen in FIG. 6C, where distal tip 17 is disposed away from plane D-D, in order to cause such a non-planar (e.g., three-dimensional) extension of distal tip 17, distal tip 17 is biased in more than one direction (e.g., by bending distal tip 17 downward and to the right in FIG. 6C). In this embodiment, inner conductor 16 extends downward and towards to the right upon initial deployment of inner conductor 16. Continued deployment of inner conductor 16 causes distal tip 17 to continue to move in a spiral-like configuration and farther away from outer conductor 24 and plane D-D and into a corkscrew-, helix- or serpentine-type configuration.

As can be appreciated with respect to FIGS. 5B and 6B, areas of tissue disposed adjacent center line T3-T3 are contacted by inner conductor 16. Thus, the use of planar inner conductor 16 (FIGS. 5A-5C) and/or non-planar inner conductor 16 (FIGS. 6B and 6C) may be useful for creating a larger ablation region. Similarly and/or concomitantly, use of planar and/or non-planar inner conductor 16 may also be useful for creating an ablation region using a relatively low amount of power, as less power may be required to reach the center of the ablation region using microwave ablation device 10 of the present disclosure vis-à-vis a microwave ablation device 10' of the prior art.

A method of treating tissue using ablation device 10 is also included by the present disclosure. The method may include at least providing microwave ablation device 10, such as described above, and extending distal tip 17 of inner conductor 16 beyond a distal-most end of outer conductor 24 such that distal tip 17 extends in a spiral-like configuration having inconsistent and/or non-equivalent radii.

Various modifications may be made to the embodiments disclosed herein. Therefore, the above description should not be construed as limiting, but merely as exemplifications of various embodiments. Those skilled in the art will envision other modifications within the scope and spirit of the claims appended hereto.

The invention claimed is:

1. A medical device, comprising;
a handle portion; and
a deployable member disposed in mechanical cooperation with the handle portion, the deployable member including a distal tip and a bend disposed adjacent the distal tip, wherein the deployable member is extendable from the handle portion such that the distal tip extends in a spiral-like configuration in response to extension of the deployable member and wherein the spiral-like configuration includes non-equivalent radii and wherein a portion of the distal tip that is disposed distally of the bend is configured to deploy towards a center of the spiral-like configuration.

2. The medical device according to claim 1, wherein the deployable member is configured to deliver at least one of radiofrequency energy, microwave energy, ultrasound, cryotherapy energy and laser energy to a tissue of a patient.

3. The medical device according to claim 1, wherein the deployable member is configured to deliver energy and material to a tissue of a patient.

4. The medical device according to claim 3, wherein the deployable member is configured to deliver at least one of a material, a fluid, a chemotherapeutic agent, a saline and an electrolytic solution to a tissue of a patient.

5. The medical device according to claim 1, wherein the deployable member is configured to mark a target area within a patient.

6. The medical device according to claim 1, wherein a radius of the spiral-like configuration between the distal tip and a center line extending through the spiral-like configuration becomes smaller as the inner conductor extends beyond the outer conductor.

7. The medical device according to claim 1, wherein the deployable member is configured to extend substantially in a plane defined by the handle portion.

8. The medical device according to claim 1, wherein the deployable member is configured to extend away from a plane defined by the handle portion.

9. The medical device of claim 1, wherein a portion of the deployable member that is disposed immediately proximal of the bend and a portion of the deployable member that is disposed immediately distal of the bend form an angle of between about 5° and about 25°.

10. An ablation device, comprising:
a handle portion;

an inner conductor extending distally from the handle portion and including a length, a proximal portion, a distal tip and a bend disposed adjacent the distal tip; and an outer conductor surrounding the inner conductor and extending at least partially along the length of the inner conductor, the outer conductor defining a longitudinal axis, wherein at least the distal tip of the inner conductor is extendable distally beyond a distal-most end of the outer conductor, and wherein the distal tip extends in a spiral-like configuration in response to extension of the inner conductor, and wherein the spiral-like configuration includes non-equivalent radii, and wherein a portion of the distal tip that is disposed distally of the bend is configured to deploy towards a center of the spiral-like configuration.

11. The ablation device according to claim 10, wherein a radius of the spiral-like configuration between the distal tip and a center line extending through the spiral-like configuration becomes smaller as the inner conductor extends beyond the outer conductor.

12. The ablation device according to claim 10, wherein the outer conductor defines a plane that is parallel to the longitudinal axis and wherein the distal tip of the inner conductor is extendable substantially along the plane.

13. The ablation device according to claim 10, wherein the outer conductor defines a plane that is parallel to the longitudinal axis and wherein the distal tip of the inner conductor is extendable away from the plane.

14. The ablation device according to claim 10, wherein the distal tip of the inner conductor is biased away from the longitudinal axis.

15. The ablation device according to claim 10, wherein the inner conductor is rotatable about the longitudinal axis with respect to the handle portion.

16. The ablation device according to claim 10, further including a dielectric material disposed between the inner conductor and the outer conductor.

17. The ablation device according to claim 10, wherein at least a portion of the inner conductor is advanceable substantially along the longitudinal axis with respect to the outer conductor.

18. The ablation device of claim 10, wherein a portion of the inner conductor that is disposed immediately proximal of the bend and a portion of the inner conductor that is disposed immediately distal of the bend form an angle of between about 5° and about 25°.

19. A method of treating tissue, comprising:
providing an ablation device, including:
a handle portion;
an inner conductor extending distally from the handle portion and including a length, a proximal portion, a distal tip and a bend disposed adjacent the distal tip; and
an outer conductor surrounding the inner conductor and extending at least partially along the length of the inner conductor, the outer conductor defining a longitudinal axis; and
extending the distal tip of the inner conductor beyond a distal-most end of the outer conductor such that the distal tip extends in a spiral-like configuration having non-equivalent radii and such that a portion of the distal tip that is disposed distally of the bend extends towards a center of the spiral-like configuration.

20. The method according to claim 19, wherein a radius of the spiral-like configuration between the distal tip and a center line extending through the spiral-like configuration becomes smaller as the inner conductor extends beyond the outer conductor.

21. The method according to claim 19, further including a dielectric material disposed between the inner conductor and the outer conductor.

22. The method according to claim 19, wherein the outer conductor defines a plane that is parallel to the longitudinal axis and wherein the distal tip of the inner conductor is extendable away from the plane.

23. The method according to claim 19, wherein the distal tip of the inner conductor is biased away from the longitudinal axis.

24. The method according to claim 19, further including rotating the inner conductor about the longitudinal axis with respect to the handle portion.

25. The method of claim 19, wherein a portion of the inner conductor that is disposed immediately proximal of the bend and a portion of the inner conductor that is disposed immediately distal of the bend form an angle of between about 5° and about 25°.

26. An ablation device for treating tissue, the ablation device comprising;
an outer conductor defining a longitudinal axis;
a dielectric material retained within the outer conductor; and
an inner conductor slidably supported within the dielectric material and extendable from a distal end of the outer conductor and a distal end of the dielectric material, the inner conductor including a bend disposed adjacent a distal tip thereof,
wherein a distal portion of the inner conductor is biased to a spiral-like configuration having a varying radius along an entire length thereof,
and wherein a portion of the distal tip that is disposed distally of the bend is configured to deploy towards a center of the spiral-like configuration.

27. The ablation device of claim 26, wherein a portion of the inner conductor that is disposed immediately proximal of the bend and a portion of the inner conductor that is disposed immediately distal of the bend form an angle of between about 5° and about 25°.

* * * * *